US012661058B2

(12) United States Patent　(10) Patent No.:　US 12,661,058 B2
Sota et al.　(45) Date of Patent:　Jun. 23, 2026

(54) DETERMINATION DEVICE, DETERMINATION METHOD, AND PROGRAM

(71) Applicants:HUMAN ENGINEERING CO., LTD, Shizuoka (JP); WASEDA UNIVERSITY, Tokyo (JP); SHINSHU UNIVERSITY, Nagano (JP); Q'SFIX CO., LTD., Tokyo (JP)

(72) Inventors: Takayuki Sota, Tokyo (JP); Atsushi Nakamura, Tokyo (JP); Ayaka Murata, Tokyo (JP); Hiroshi Koga, Nagano (JP); Akane Minagawa, Nagano (JP)

(73) Assignee: HUMAN ENGINEERING CO., LTD (JP)

( * ) Notice: Subject to any disclaimer, the term of this patent is extended or adjusted under 35 U.S.C. 154(b) by 279 days.

(21) Appl. No.: 18/566,351

(22) PCT Filed: Jun. 4, 2021

(86) PCT No.: PCT/JP2021/021411
　§ 371 (c)(1),
　(2) Date: Dec. 1, 2023

(87) PCT Pub. No.: WO2022/254707
　PCT Pub. Date: Dec. 8, 2022

(65) Prior Publication Data
　US 2024/0245347 A1　Jul. 25, 2024

(51) Int. Cl.
　*G06T 7/00*　(2017.01)
　*A61B 5/00*　(2006.01)
　(Continued)

(52) U.S. Cl.
　CPC ............ *A61B 5/449* (2013.01); *A61B 5/1032* (2013.01); *G06T 5/00* (2013.01); *G06T 7/0012* (2013.01);
　(Continued)

(58) Field of Classification Search
　CPC ....... A61B 5/449; A61B 5/1032; A61B 5/443; A61B 5/444; A61B 2576/00;
　(Continued)

(56) References Cited

U.S. PATENT DOCUMENTS

2012/0041275 A1 *　2/2012　Sota ........................ G06T 7/136
　600/300
2012/0268462 A1 *　10/2012　Sota ........................ A61B 5/449
　345/419
(Continued)

FOREIGN PATENT DOCUMENTS

JP　2011-130897 A　7/2011
JP　2016-174671 A　10/2016
(Continued)

OTHER PUBLICATIONS

Office Action in related Australian Application 2021448510 dated Oct. 22, 2024, pp. 1-6.
(Continued)

*Primary Examiner* — Van D Huynh
(74) *Attorney, Agent, or Firm* — Womble Bond Dickinson (US) LLP

(57)　ABSTRACT

A determination device 1 includes: an acquisition unit 21 that acquires digital color image data 11 of a region of interest in melanonychia of a subject; a calculation unit 23 that calculates an indicator value 12 from variation in RGB values of each pixel of the digital color image data 11; and an output unit 24 that outputs a result of determining that the melanonychia is malignant if the indicator value 12 is higher
(Continued)

than a threshold value and determining that the melanonychia is benign if the indicator value 12 is lower than the threshold value.

9 Claims, 5 Drawing Sheets

(51) Int. Cl.
    *A61B 5/103*         (2006.01)
    *G06T 5/00*          (2006.01)
    *G06T 7/90*          (2017.01)

(52) U.S. Cl.
    CPC ...... *G06T 7/90* (2017.01); *G06T 2207/10024*
        (2013.01); *G06T 2207/30088* (2013.01); *G06T*
        *2207/30096* (2013.01)

(58) Field of Classification Search
    CPC ....... A61B 5/0077; G06T 5/00; G06T 7/0012;
        G06T 7/90; G06T 2207/10024; G06T
        2207/30088; G06T 2207/30096; G06T
        2207/10056; G01J 3/46
    See application file for complete search history.

(56) References Cited

U.S. PATENT DOCUMENTS

2020/0311939 A1\*  10/2020  Sota ...................... A61B 5/441
2020/0320683 A1    10/2020  Horiuchi et al.

FOREIGN PATENT DOCUMENTS

JP      2010-252895 A   11/2020
WO    2018/216680 A1  11/2018

OTHER PUBLICATIONS

The International Search Report and Written Opinion for International Application No. PCT/JP2021/021411 mailed on Jul. 6, 2021.
Koga et al., "Automated evaluation of dermoscopic images of longitudinal melanonychia: Proposition of a discrimination index for detecting early nail apparatus melanoma," The Journal of Dermatology, 2014, pp. 867-871, vol. 41, Japanese Dermatological Association (doi: 10.1111/1346-8138.12593).
Anonymous, "open cv—How to Compute RGB Image Standard Deviation from per Channel values—Stack Overflow," Internet search Jul. 28, 2018 URL:https://stackoverflow.com/questions/51573399/how-to-compute-rgbimage-standard-deviation-from-per-channel-values.
EP 21 94 4201, Extended European Search Report, Feb. 21, 2025.

\* cited by examiner (a)

(b)

DETERMINATION DEVICE, DETERMINATION METHOD, AND PROGRAM

CROSS-REFERENCE TO RELATED APPLICATIONS

This application is a national phase entry of International Application No. PCT/JP2021/021411 filed on Jun. 4, 2021, the contents of which are incorporated herein by reference in its entirety.

TECHNICAL FIELD

The present invention relates to a determination device, a determination method, and a program.

BACKGROUND ART

Under normal conditions, melanocytes present in a nail matrix are inactive and do not produce melanin. Regardless of whether the melanocytes are cancerous, the melanocytes may begin to produce melanin. As the nail grows, the produced melanin forms a pattern called melanonychia. Melanonychia when the melanocytes are not cancerous is considered to be a benign nevus. It is thought that determination as to whether the melanocytes present in the nail matrix are cancerous is possible from the melanonychia pattern.

However, considerable experience is required to visually determine whether the pattern is benign or malignant using a dermoscope. In the case of malignant melanoma, a biopsy is generally performed. A biopsy is burdensome to a patient and does not lead to benefits for the patient. Due to these factors, it is thought that a definitive diagnosis of melanonychia is difficult and these factors result in a poor prognosis. Therefore, the realization of a non-invasive and objective method for determining melanonychia is strongly required from clinical settings.

Therefore, the inventors have invented a non-invasive and objective method for determining whether melanonychia is benign or malignant (see, for example, Patent Literature 1 and Patent Literature 2). In Patent Literature 1, RGB parameter values of each pixel in a digital color image of the melanonychia are regarded as a three-dimensional vector having those three values as components, and a threshold value is obtained from an appearance probability of each angle formed between each three-dimensional vector and a reference vector. In Patent Literature 2, a latitudinal variable and a longitudinal variable in RGB space of a three-dimensional vector are obtained, and indicator values are obtained from the distribution of points defined based on the obtained latitudinal variable and longitudinal variable. In Patent Literature 2, the indicator values are further distinguished based on a threshold value to determine whether melanonychia is malignant or benign.

In the methods disclosed in Patent Literatures 1 and 2, a result of determining whether the melanonychia is benign or malignant may change when a plurality of inspections are performed over time. Therefore, the inventors proposed a determination method taking the progress of the indicator values of each inspection into consideration (Patent Literature 3).

In addition, the inventors invented a method of analyzing the melanonychia or the like for a diagnosis of a skin disease (see, for example, Patent Literature 4). Patent Literature 4 discloses that the color balance of a color digital image of subject's melanonychia or the like is adjusted by performing a chromatic adaptation transformation. Patent Literature 4 makes it possible to obtain a color digital image without depending on the person carrying out the inspection or an imaging device by correcting the hue of an image in a dermoscopy inspection.

CITATION LIST

Patent Literature

PTL 1: JP 2010-252895 A
PTL 2: JP 2011-130897 A
PTL 3: JP 2016-174671 A
PTL 4: WO 2018/216680

SUMMARY OF THE INVENTION

Technical Problem

There is a demand for development of a method of more quickly and appropriately determining whether melanonychia is benign or malignant. In the methods disclosed in Patent Literatures 1 and 2, the determination result may change over time. In the method disclosed in Patent Literature 3, since the determination is made by considering the progress of the indicator values of each inspection, it may take time to determine whether a biopsy is necessary.

The present invention has been devised in consideration of the above problems, and an object of the present invention is to provide a technique capable of more quickly and appropriately determining whether melanonychia is benign or malignant.

Solution to Problem

A determination device of one aspect of the present invention includes: an acquisition unit that acquires digital color image data of a region of interest in melanonychia of a subject; a calculation unit that calculates an indicator value from variation in RGB values of each pixel of the digital color image data; and an output unit that outputs a result of determining that the melanonychia is malignant if the indicator value is higher than a threshold value and determining that the melanonychia is benign if the indicator value is lower than the threshold value.

A determination method of one aspect of the present invention includes: a computer acquiring digital color image data of a region of interest in melanonychia of a subject; the computer calculating an indicator value from variation in RGB values of each pixel of the digital color image data; and the computer outputting a result of determining that the melanonychia is malignant if the indicator value is higher than a threshold value and determining that the melanonychia is benign if the indicator value is lower than the threshold value.

One aspect of the present invention provides a program for causing a computer to function as the determination device.

Advantageous Effects of the Invention

According to the present invention, it is possible to provide a technique capable of more quickly and appropriately determining whether melanonychia is benign or malignant.

DESCRIPTION OF EMBODIMENT

Figure 1:
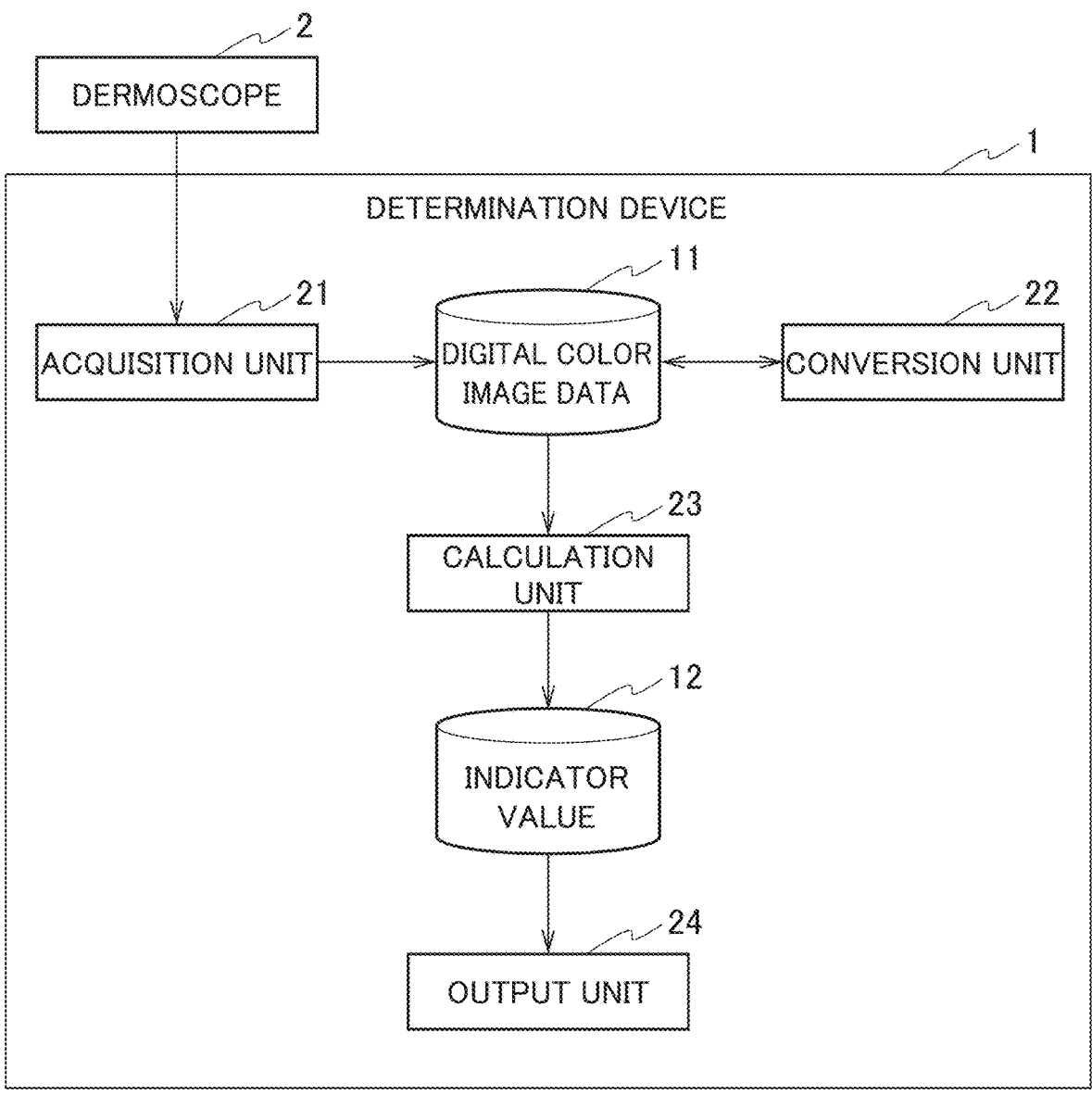
FIG. 1 is a diagram for explaining functional blocks of a determination device according to an embodiment of the present invention.

An embodiment of the present invention will be described below with reference to the drawings. In the description of the drawings, the same parts are denoted with the same reference numerals, and the description thereof is omitted.
(Determination Device)

Figure 2:
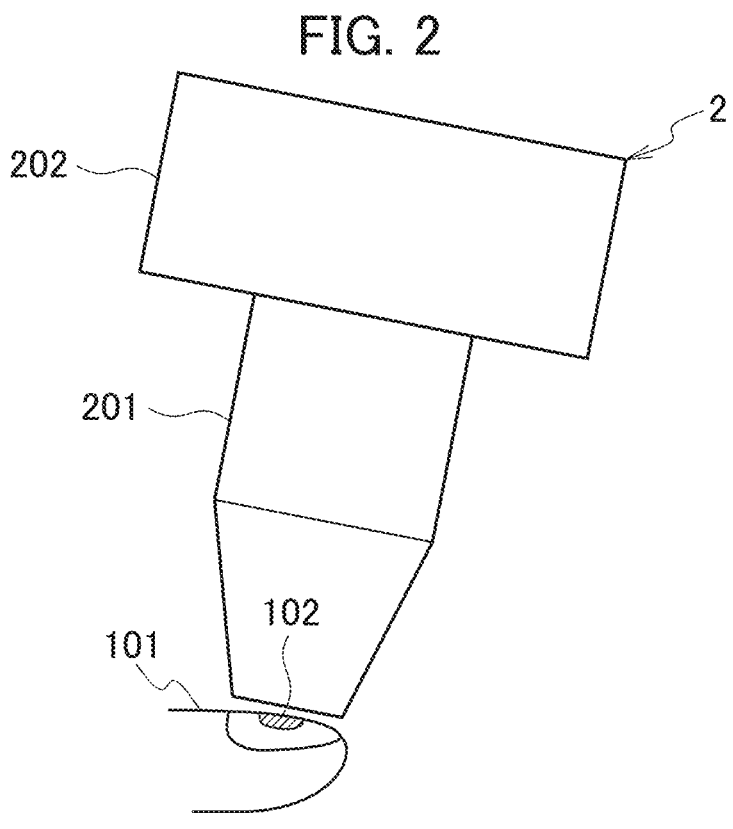
FIG. 2 is a diagram for explaining how an image of melanonychia is captured using a dermoscope.
Figure 3:
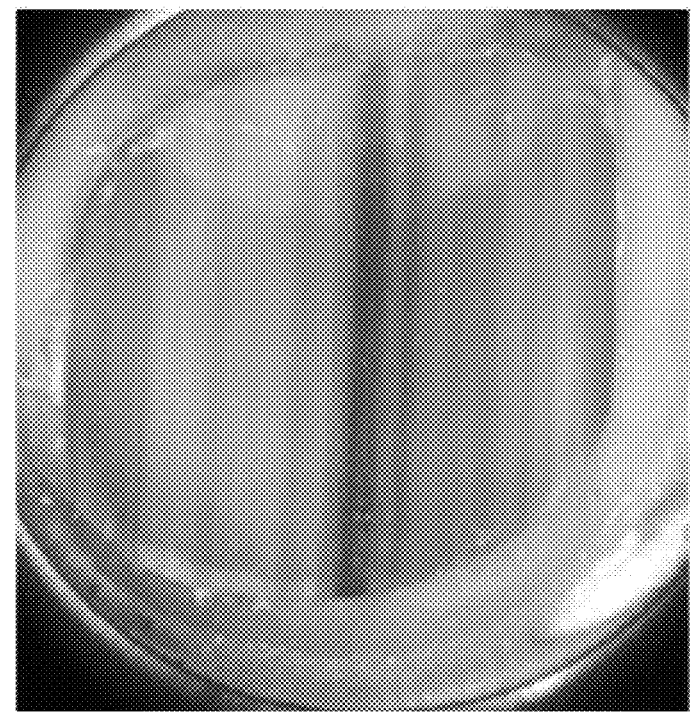
FIG. 3 shows an example of melanonychia.

A determination device 1 according to an embodiment of the present invention shown in FIG. 1 calculates an indicator value based on image data obtained by capturing an image of melanonychia 102 that has occurred on a subject's nail 101 using a dermoscope 2 as shown in FIGS. 2 and 3. The determination device 1 compares the indicator value with a threshold value and determines whether the melanonychia 102 is malignant or benign. The result of the determination performed by the determination device 1 supports a diagnosis of the melanonychia 102 performed by a user such as a physician.

The determination device 1 is provided with pieces of data of digital color image data 11 and an indicator value 12 and the functions of an acquisition unit 21, a conversion unit 22, a calculation unit 23, and an output unit 24. The pieces of data are stored in a memory 902 or a storage 903. The functions are implemented by a CPU 901.

The digital color image data 11 is data of a region of interest in the subject's melanonychia 102. The digital color image data 11 is captured by using, for example, the dermoscope 2 with a camera function. The region of interest (ROI) is a portion including the subject's melanonychia 102 or a portion of the subject's melanonychia 102. The digital color image data 11 is data obtained by associating each pixel corresponding to the region of interest with a color value represented by the pixel and digitizing the region of interest. In the embodiment of the present invention, the digital color image data 11 is obtained by associating each pixel in the region with a color value of each of red, green, and blue (RGB).

The indicator value 12 is calculated from variation in the RGB values of each pixel of the digital color image data 11. The indicator value 12 is an indicator for determining whether the region of interest is benign or malignant. The indicator value is also referred to as a discrimination index (DI) value.

The acquisition unit 21 acquires the digital color image data 11 of the region of interest in the subject's melanonychia 102. The acquisition unit 21 acquires, from the dermoscope 2, digital-format image data obtained by capturing an image of a subject's nail 101 part. The acquisition unit 21 generates the digital color image data 11 by cutting out the region of interest from the acquired image data. The region of interest may be specified by a user or by a prescribed program.

The conversion unit 22 adjusts the color balance of the digital color image data 11 by performing a chromatic adaptation transformation and updates the digital color image data 11. The conversion unit 22 adjusts the color balance, and corrects and standardizes the hue of the digital color image data 11.

Generally, in a dermoscopy inspection, the color balance may differ due to the imaging environment using a dermoscope, the image processing engine used for the dermoscope, and the like. For example, the imaging environment using the dermoscope may be influenced by the spectral distribution of illumination light, which varies depending on the device used for the dermoscopy inspection, or the like. Therefore, the conversion unit 22 eliminates the difference in the color balance caused by the imaging environment and the image processing engine in the inspection by adjusting the color balance. The conversion unit 22 can accurately determine the melanonychia 102 by adjusting the color balance.

The conversion unit 22 adjusts the hue of each piece of digital color image data such that the appearance of white becomes constant in digital color image data captured by using various devices. The conversion unit 22 standardizes the hue of the digital color image data obtained under various conditions by converting an average chromaticity coordinate of prescribed pixels in the data to a preset reference chromaticity coordinate. The details are disclosed in Patent Literature 4. Patent Literature 4 is incorporated herein.

The calculation unit 23 calculates the indicator value 12 from the variation in RGB values of each pixel of the digital color image data 11. The calculation unit 23 preferably uses digital color image data 11 of which the hue has been adjusted by the conversion unit 22.

The calculation unit 23 calculates the indicator value 12 from variation in the R value, variation in the G value, and variation in the B value of each pixel. The indicator value 12 is calculated by normalizing the sum of the standard deviation of each of the R value, the G value, and the B value of each pixel of the digital color image data 11 by the number of pixels.

The calculation unit 23 calculates the indicator value 12 from formula (1).

$$DI = \left[ \frac{1}{N} \left\{ \sum_{i=1}^{N} (R_i - \overline{R})^2 + \sum_{i=1}^{N} (G_i - \overline{G})^2 + \sum_{i=1}^{N} (B_i - \overline{B})^2 \right\} \right]^{1/2} \qquad \text{Formula (1)}$$

DI: Indicator value

N: Number of pixels in digital color image data $R_i$, $G_i$, $B_i$: Values of each of RGB of pixel i $\overline{R}$, $\overline{G}$, $\overline{B}$: Average value of values of each of RGB of digital color image data The calculation unit 23 calculates a higher indicator value 12 as the diversity of the colors in the digital color image data 11 increases. The calculation unit 23 calculates a lower indicator value as the diversity of the colors in the digital color image data 11 decreases.

The output unit 24 determines that the melanonychia 102 is malignant if the indicator value is higher than the threshold value, and that the melanonychia 102 is benign if the indicator value is lower than the threshold value, and outputs the determination result. When each value of RGB is represented in 8 bits and has a range of 0 to 255, the threshold value is, for example, 40.

The determination result output by the output unit 24 is not the final determination made by the physician but one element for supporting the physician's determination. For example, if the indicator value 12 is higher than the threshold value, there is a high possibility that the melanonychia 102 is malignant, and therefore the output unit 24 may display a message prompting a biopsy. If the indicator value is lower than the threshold value, there is a high possibility that the melanonychia 102 is benign, and therefore the output unit 24 may display a message such as no biopsy is required or a follow-up observation is advised.

Figure 4:
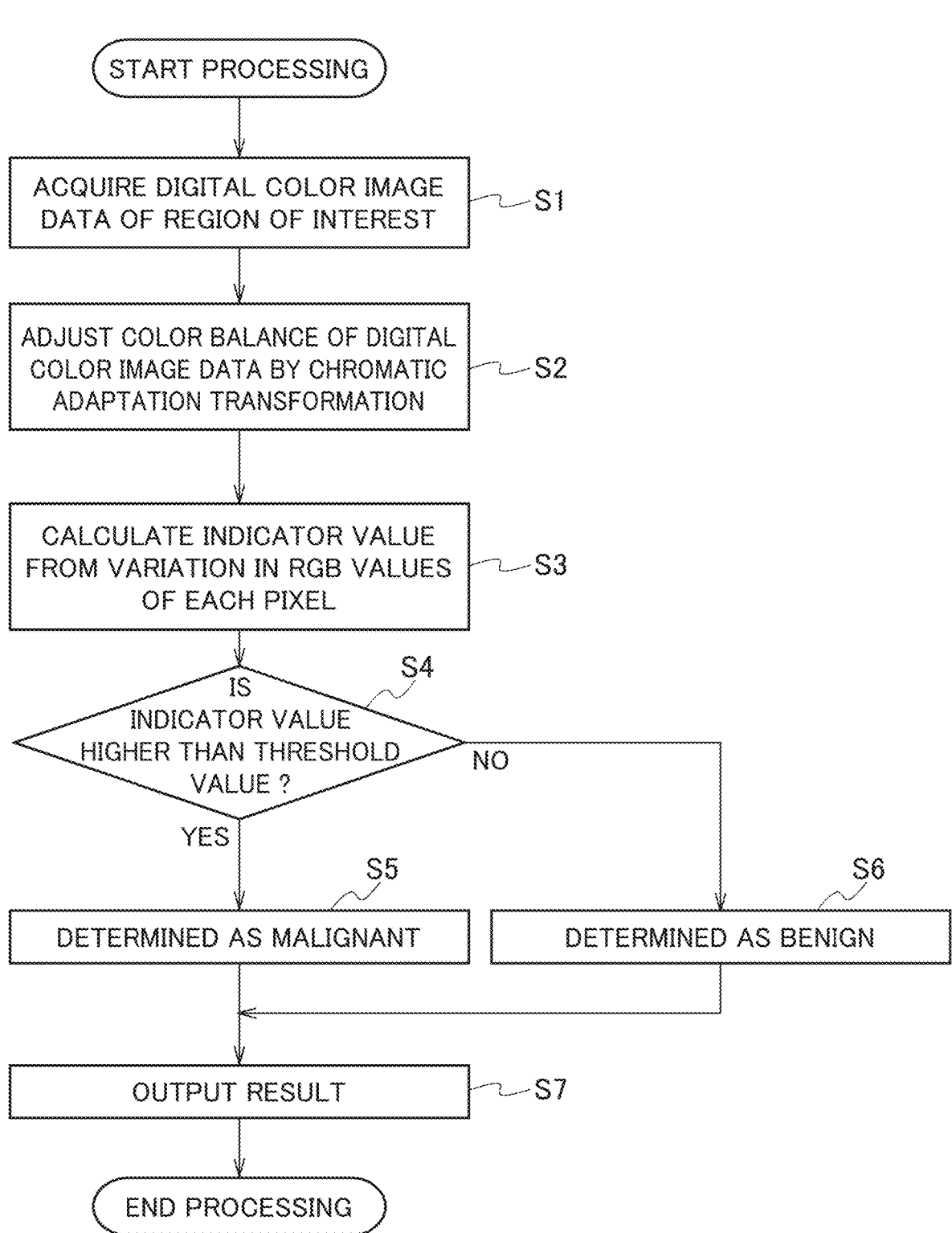
FIG. 4 is a flowchart for explaining determination processing performed by a determination device.

With reference to FIG. 4, a determination method performed by the determination device 1 according to the embodiment of the present invention will be described. The processing sequence shown in FIG. 4 is an example, and the sequence is not limited thereto.

In step S1, the determination device 1 acquires the digital color image data 11 of the region of interest of the subject's melanonychia 102. In step S2, the determination device 1 adjusts the color balance of the digital color image data 11 acquired in step S1 by performing the chromatic adaptation transformation and updates the data.

In step S3, the determination device 1 calculates the indicator value from the variation in RGB values of each pixel of the digital color image data 11 of which the color balance has been adjusted in step S2.

In step S4, the determination device 1 compares the indicator value calculated in step S3 with the threshold value to determine whether the melanonychia is malignant or benign. If the indicator value is higher than the threshold value, in step S5, the determination device 1 determines that there is a high possibility that the melanonychia 102 imaged as the digital color image data 11 is malignant. If the indicator value is lower than the threshold value, in step S6, the determination device 1 determines that there is a high possibility that the melanonychia 102 imaged as the digital color image data 11 is benign.

In step S7, the determination device 1 outputs the determination result in step S5 or step S6 to an output device such as a display.

The results of determination performed by the determination device 1 according to the embodiment of the present invention will be described with reference to FIG. 5. Both of FIGS. 5(*a*) and 5(*b*) show receiver operating characteristic (ROC) curves in which the region of interest of the melanonychia 102 is determined. The vertical axis of the ROC curve is a true positive rate and the horizontal axis of the curve is a false positive rate. The area under the curve (AUC) is the area of the portion below the ROC curve. It is shown that the discrimination capability increases as the AUC value approaches 1.

Figure 5:
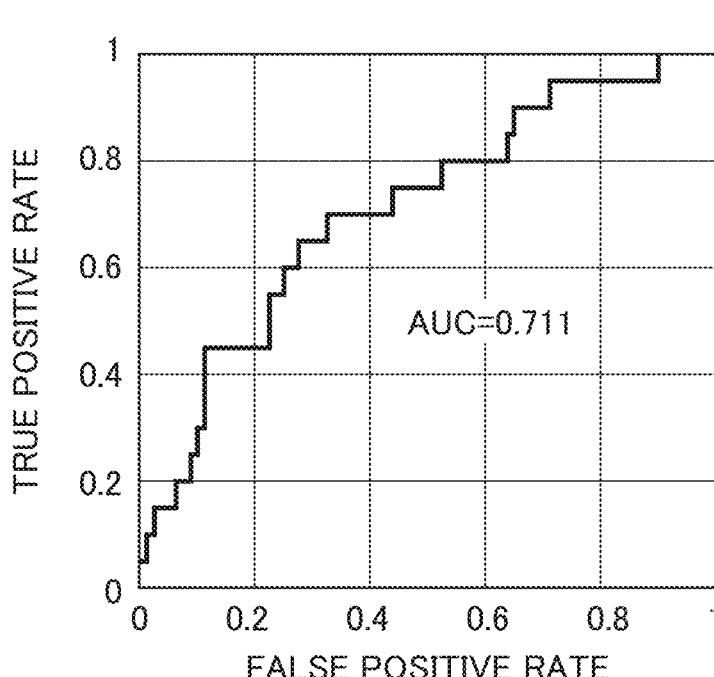
FIG. 5 is a diagram for explaining a result of determination performed by the determination device according to the embodiment of the present invention.
Figure 5:
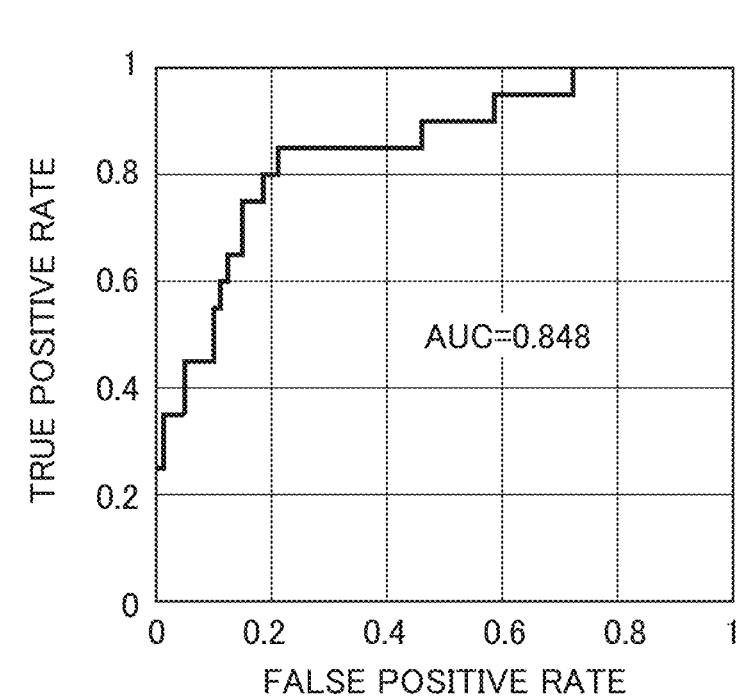
Figure 6:
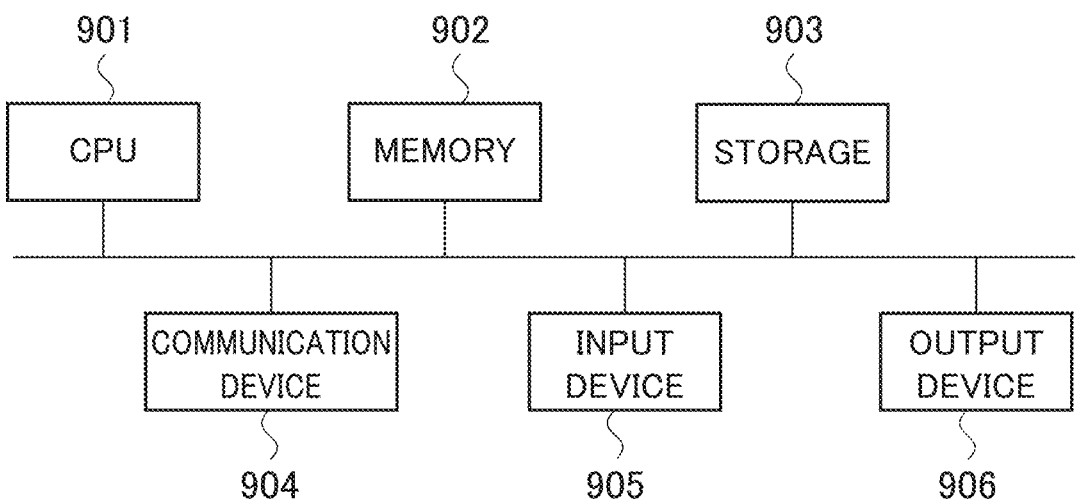
FIG. 6 is a diagram for explaining a hardware configuration of a computer used for a determination device.

FIG. 5(*a*) shows the result of determination by means of the methods disclosed in Patent Literature 1 and Patent Literature 2. FIG. 5(*b*) shows the result of determination performed by the determination device 1 according to the embodiment of the present invention. The results of determination shown in FIGS. 5(*a*) and 5(*b*) are obtained by performing determination for 100 cases of melanonychia. Out of the 100 cases, 80 cases are determined to be benign and 20 cases are determined to be malignant according to the physician's diagnosis. The true positive rate and false positive rate are calculated from the determination results according to each determination method and a correct label according to the physician's diagnosis result.

In the conventional determination result shown in FIG. 5(*a*), the AUC is 0.711. Meanwhile, in the determination result according to the embodiment of the present invention shown in FIG. 5(*b*), the AUC is 0.848, and it can be seen that the result exhibited a higher discrimination capability than that exhibited by the conventional determination result.

In a determination result using deep learning by means of a convolutional neural network, the AUC of the ROC curve is 0.621 (J. K. Winkler et al., European Journal of Cancer 127 (2020) e21-29). Meanwhile, in the determination result obtained by the determination device 1 according to the embodiment of the present invention, the AUC is 0.848. It can be seen that the determination device 1 has a higher discrimination capability than that exhibited by the determination result obtained by deep learning.

Further, the sensitivity and the specificity of the detection of malignancy (melanoma) performed by the determination device 1 according to the embodiment of the present invention are 0.85 and 0.79, respectively. In contrast, the average sensitivity of eight dermatologists is 0.66 and the average specificity is 0.98. The average sensitivity of eight non-dermatologists is 0.46 and the average specificity is 0.97. This reveals that, although the specificity is higher in the determination performed by the dermatologists and non-dermatologists, the sensitivity tends to be higher in the determination performed by the determination device 1. The determination device 1 can appropriately determine malignancy and prompt a biopsy for the subject immediately compared with a determination made by a physician.

When the determination as to whether a biopsy is necessary performed by means of the majority decision of three experts with a wealth of experience in treating nail melanoma is assumed to be the correct label, the determination result by the determination device 1 exhibits a sensitivity of 0.95, a specificity of 0.82, and an AUC of 0.92. The determination device 1 can determine whether the melanonychia is benign or malignant at the same level as a physician who is an expert in nail melanoma.

The determination device 1 according to the embodiment of the present invention calculates the indicator value from the variation in RGB values of each pixel of the digital color image data 11 obtained by capturing an image of the region of interest of the melanonychia 102 by using the dermoscope 2, and determines whether the melanonychia 102 is benign or malignant. According to the knowledge by the inventors, "the essence of malignant melanoma is morphological disorder including color tone", and therefore, the determination device 1 calculates an indicator value considering the diversity of color tones in the region of interest, and thereby can calculate an indicator value suitable for the determination of the melanonychia 102.

In addition, the determination device 1 can suppress the influence on the indicator value due to differences in imaging devices, persons who capture images, imaging environments, and the like by the conversion unit 22 adjusting the color balance. The indicator value calculated by the determination device 1 has high robustness with respect to input images and enables objective evaluation of the melanonychia 102.

For the determination device 1 of the present embodiment described above, for example, a general-purpose computer system is used which includes a central processing unit (CPU, processor) 901, a memory 902, a storage 903 (HDD: hard disk drive, SSD: solid state drive), a communication device 904, an input device 905, and an output device 906.

In this computer system, each function of the determination device 1 is realized by the CPU 901 executing a program loaded into the memory 902.

The determination device 1 may be implemented by one computer or a plurality of computers. The determination device 1 may be a virtual machine implemented on a computer.

The program of the determination device 1 may be stored on a computer-readable recording medium such as an HDD, an SSD, a Universal Serial Bus (USB) memory, a compact disc (CD), or a digital versatile disc (DVD), or may be distributed via a network.

It should be noted that the present invention is not limited to the above embodiment, and various modifications can be made within the scope of the invention.

REFERENCE SIGNS LIST

1 Determination device
2 Dermoscope
11 Digital color image data
12 Indicator value
21 Acquisition unit
22 Conversion unit
23 Calculation unit
24 Output unit
901 CPU
902 Memory
903 Storage
904 Communication device
905 Input device
906 Output device

What is claimed is:

1. A determination device comprising:
a processor configured to:
acquire digital color image data of a region of interest in melanonychia of a subject;
calculates an indicator value based on variation in R value, variation in G value, and variation in B value of each pixel of the digital color image data; and
output a result of determining that the melanonychia is malignant if the indicator value is higher than a threshold value and determining that the melanonychia is benign if the indicator value is lower than the threshold value.

2. The determination device according to claim 1, the processor is further configured to:
adjust a color balance of the digital color image data by performing a chromatic adaptation transformation, wherein
calculate the indicator value from the digital color image data after the chromatic adaptation transformation of the region of interest.

3. The determination device according to claim 1, wherein the processor is further configured to calculate the indicator value based on:

$$DI = \left[ \frac{1}{N} \left\{ \sum\nolimits_{i=1}^{N} (R_i - \bar{R})^2 + \sum\nolimits_{i=1}^{N} (G_i - \bar{G})^2 + \sum\nolimits_{i=1}^{N} (B_i - \bar{B})^2 \right\} \right]^{1/2},$$

wherein DI corresponds to an indicator value, N corresponds to a number of pixels in digital color image data $R_i$, $G_i$, $B_i$ correspond to values of each of RGB of pixel i, and $\bar{R}$, $\bar{G}$, $\bar{B}$ correspond to an average value of values of each of RGB of digital color image data.

4. The determination device according to claim 2, wherein the processor is further configured to calculate the indicator value based on:

$$DI = \left[ \frac{1}{N} \left\{ \sum\nolimits_{i=1}^{N} (R_i - \bar{R})^2 + \sum\nolimits_{i=1}^{N} (G_i - \bar{G})^2 + \sum\nolimits_{i=1}^{N} (B_i - \bar{B})^2 \right\} \right]^{1/2},$$

wherein DI corresponds to an indicator value, N corresponds to a number of pixels in digital color image data $R_i$, $G_i$, $B_i$ correspond to values of each of RGB of pixel i, and $\bar{R}$, $\bar{G}$, $\bar{B}$ correspond to an average value of values of each of RGB of digital color image data.

5. A determination method comprising:
a computer acquiring digital color image data of a region of interest in melanonychia of a subject;
the computer calculating an indicator value based on variation in R value, variation in G value, and variation in B value of each pixel of the digital color image data; and
the computer outputting a result of determining that the melanonychia is malignant if the indicator value is higher than a threshold value and determining that the melanonychia is benign if the indicator value is lower than the threshold value.

6. A non-transitory computer-readable storage medium storing a program for causing a computer to function as the determination device according to claim 1.

7. A non-transitory computer-readable storage medium storing a program for causing a computer to function as the determination device according to claim 2.

8. A non-transitory computer-readable storage medium storing a program for causing a computer to function as the determination device according to claim 3.

9. A non-transitory computer-readable storage medium storing a program for causing a computer to function as the determination device according to claim 4.

* * * * *